US009385768B2

(12) United States Patent
De Haan (10) Patent No.: US 9,385,768 B2
(45) Date of Patent: Jul. 5, 2016

(54) DEVICE AND METHOD FOR EXTRACTING PHYSIOLOGICAL INFORMATION

(71) Applicant: KONINKLIJKE PHILIPS N.V., Eindhoven (NL)

(72) Inventor: Gerard De Haan, Helmond (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/435,321

(22) PCT Filed: Oct. 18, 2013

(86) PCT No.: PCT/IB2013/059446
§ 371 (c)(1),
(2) Date: Apr. 13, 2015

(87) PCT Pub. No.: WO2014/068436
PCT Pub. Date: May 8, 2014

(65) Prior Publication Data
US 2015/0236740 A1 Aug. 20, 2015

Related U.S. Application Data (60) Provisional application No. 61/721,546, filed on Nov. 2, 2012.

(51) Int. Cl.
*H04L 27/06* (2006.01)
*H04B 1/16* (2006.01)

(52) U.S. Cl.
CPC ........................................ *H04B 1/16* (2013.01)

(58) Field of Classification Search
CPC .. A61B 5/0095; A61B 8/5292; A61B 8/4281; A61B 8/4416; G06T 11/003; H04L 25/067; H04L 1/0045; H04L 27/2647; H04L 1/005; H04L 1/0054; H04L 1/20; H04N 5/4401; H04B 1/30; H04B 1/28

USPC .................................. 375/340, 316, 219, 295
See application file for complete search history.

(56) References Cited

U.S. PATENT DOCUMENTS

2006/0111623 A1 5/2006 Stetson
2011/0251493 A1 10/2011 Poh et al.
(Continued)

FOREIGN PATENT DOCUMENTS

WO 2008141306 A1 11/2008
WO 2013030739 A1 3/2013
WO 2014024104 A1 2/2014

OTHER PUBLICATIONS

Verkruysse et al, "Remote Plethysmographic Imaging Using Ambient Light", Optics Express, Optical Society of America, vol. 16, No. 26, 2008, p. 21434-21445.
(Continued)

*Primary Examiner* — Zewdu Kassa (57) ABSTRACT

The present invention relates to a device and a method for extracting physiological information from remotely detected electromagnetic radiation (14) emitted or reflected by a subject. A data stream (24) derived from detected electromagnetic radiation (14) is received, the data stream (24) comprising a sequence of signal samples representing a region of interest (58) exhibiting a continuous or discrete characteristic signal including physiological information indicative of at least one at least partially periodic vital signal (20), and being comprised of at least two wavelength components. The device further comprises a transforming unit for providing coefficient components from the at least two wavelength components and a coefficient selection unit for selecting the coefficient component which is used for calculating the desired signal component used for determining the physiological information.

16 Claims, 5 Drawing Sheets

(56) References Cited

U.S. PATENT DOCUMENTS

2011/0311119 A1    12/2011   Jeanne et al.
2012/0195486 A1     8/2012   Kirenko et al.
2013/0172675 A1*    7/2013   Yamazaki ............... H04N 9/643
                                                          600/109
2014/0249414 A1*    9/2014   Herzog ................ A61B 5/0095
                                                          600/440

OTHER PUBLICATIONS

Poh et al, "Non-Contact, Automated Cardiac Pulse Measurements Using Video Imaging and Blind Source Separation", Optics Express, vol. 18, No. 10, 2010, pp. A 10762-A 10774.

Lewandowski et al, "Measuring Pulse Rate With a Webcam—A Non-Contact Method for Evaluating Cardiac Activity", Proceedings of the Federated Conference on Computer Science and Information Systems, 2011, p. 405-410.

Verkruijsse et al, "A Novel Biometric Signature: Multi-Site, Remote (>100M) Photo Plethysmography Using Ambient Light", Technical Note PR-TN 2010/00097, March 1, 2010, Pages.

Sahindrakar, "Improviong Motion Robustness of Contact-Less Monitoring of Heart Rate Using Video Analysis", XP055051521, University of Technology, Eindhoven, NL, Aug. 24, 2011, p. 1-52.

Rabiner et al, "Theory and Application of Digital Signal Processing", Prentice-Hall, ISBN 0-13-914101-4, 1975, pp. 63-67.

\* cited by examiner

DEVICE AND METHOD FOR EXTRACTING PHYSIOLOGICAL INFORMATION

CROSS-REFERENCE TO PRIOR APPLICATIONS

This application is the U.S. National Phase application under 35 U.S.C. §371 of International Application No. PCT/IB2013/059446, filed on Oct. 18, 2013, which claims the benefit of U.S. Provisional Patent Application No. 61/721,546, filed on Nov. 2, 2012. These applications are hereby incorporated by reference herein.

FIELD OF THE INVENTION

The present invention relates to a device and method for extracting physiological information from remotely detected electromagnetic radiation emitted or reflected by a subject, wherein the physiological information is embedded in a data stream comprising a sequence of signal samples representing a region of interest exhibiting a continuous or discrete characteristic signal including physiological information indicative of at least one at least partially periodic vital signal.

BACKGROUND OF THE INVENTION

US 2011/0251493 A1 discloses a method for measuring physiological parameters comprising:
capturing a sequence of images of a human face;
identifying location of the face in a frame of the captured images and establishing a region of interest including the face;
separating pixels in the region of interest in a frame into at least two channel values forming raw traces over time;
decomposing the raw traces into at least two independent source signals; and
processing at least one of the source signals to obtain a physiological parameter.

The document further discloses several refinements of the method. In particular, the use of remote photoplethysmographic (PPG) analyses is envisaged. Photoplethysmography is a commonly known optical measurement approach which can be used to detect blood volume changes in the microvascular bed of tissue of a monitored subject. Conventional PPG approaches include so-called contact PPG. Contact PPG requires measurement components (e.g., light sources and photodetectors) which basically have to be attached to a subject's skin. Consequently, standard photoplethysmography comprises obtrusive measurements, e.g. via a transceiver unit being fixed to the subject's earlobe or fingertip. Therefore, remote PPG measurement is often experienced as being unpleasant.

Typically, a standard (or: contact) PPG device includes artificial light sources to be directly attached to an indicative surface, e.g., a skin portion, of the subject to be observed. In this manner, avoidance or reduction of adverse effects is achieved. For instance, potentially disturbing incident radiation caused by other (or: ambient) light sources and undesired object motion with respect to the light source can be addressed. Correspondingly, also the receiver or detector, e.g. at least one photodiode, is closely fixed to the subject's skin patch of interest. In case the transceiver unit is too firmly fixed to the subject so as to avoid subject movement with respect to the equipment, signal quality can be deteriorated as well, e.g. due to undesired tissue compression.

Recently, remote PPG approaches applying unobtrusive measurements have been introduced. Basically, remote photoplethysmography utilizes light sources or, in general, radiation sources, disposed remote from the subject of interest. Preferably, for some applications, even readily available existing (ambient) light sources rather than defined special-purpose light sources are utilized. For instance, artificial light sources and/or natural light sources can be exploited. Consequently, in remote PPG environments, it has to be expected that due to widely changing illumination conditions, the detected signals generally provide a very small signal-to-noise ratio. Similarly, also a detector, e.g., a camera, can be disposed remote from the subject of interest for remote PPG measurements. Therefore, remote photoplethysmographic systems and devices are considered unobtrusive and can be adapted and well suited for everyday applications. The field of application may comprise unobtrusive inpatient and outpatient monitoring and even leisure and fitness applications. In this regard, it is considered beneficial that observed subjects can enjoy a certain degree of freedom of movement during remote PPG measurement.

Consequently, compared with standard (obtrusive) photoplethysmography, remote (unobtrusive) photoplethysmography is far more susceptible to distortion and noise. Undesired subject motion with respect to the detector and/or the radiation source can excessively influence signal detection. In particular, remote photoplethysmographic devices are frequently subjected to varying overall illumination conditions. Therefore, it has to be expected that the detected signals are almost always corrupted by noise and distortion.

In addition, remote photoplethysmography measurements may suffer from so-called specular reflections in the region of interest comprising at least a portion of the subject's skin tissue. Basically, specular reflection is considered a "mirror-like" reflection of incident radiation at a surface. Specular reflections may also occur at the skin surface of a living being. This applies in particular to greasy skin portions and, generally, to subjects having considerably dark skin (high content of melanin) Since skin portions which are subjected to specular reflections basically mirror incident radiation at the skin's surface to some extend, the reflected radiation contains only a part that results from penetrating the skin tissue. Therefore, radiation with specularly reflected parts is considered not directly indicative of the desired vital signals.

In summary, remote PPG is still considered to pose major challenges to signal detection and signal processing. Since the recorded data, such as captured reflected or emitted electromagnetic radiation (e.g., recorded image frames), always comprises, besides the desired signal to be extracted therefrom, further signal components deriving from overall disturbances, for instance noise due to changing luminance conditions (including specular reflections) and relative movement between the observed subject and the detection sensor, a detailed precise extraction of the desired signals is still considered to pose major problems for existing detection approaches and processing algorithms.

As a remedy, US 2011/0251493 A1 suggests to process the derived channel data, which correspond for example to each wavelength channel provided by an RGB image detection arrangement, through an Independent Component Analysis (ICA) by which separate signal components result. In the disclosed example, these are three signal components. One of these signal components comprises the desired information related to the vital signs to be detected, for example. However, the outcome which of the signal components contains the desired information may change from case to case. In order to choose the right signal component, it is suggested to identify the signal component with a periodic signal characteristic.

This is further analyzed by transforming the time-dependent signal component into the frequency domain for analyzing the power spectrum.

Aside from being demanding with respect to computational resources, the presented method further needs significant signal length of up to one minute in order to being able to achieve a useful identification of the correct signal component by this transformation into the frequency domain. Furthermore, the presented method relies upon the assumption that the only periodic signal components after performing the ICA is the desired signal component containing the vital sign data. However, situations are possible where, for example, the aforementioned specular reflection may also result in a periodic signal component. This may be the case, by way of example, in an application where the subject that is to be monitored moves in a periodic way, for example, on an exercise device in a gym. In such an exemplary set-up, the presented method has difficulties of choosing the correct signal component after ICA and will provide erroneous vital sign data.

SUMMARY OF THE INVENTION

It is therefore an object of the present invention to provide a device and a method for extracting physiological information from remotely detected electromagnetic radiation emitted or reflected by a subject which is more efficient and less time and resource demanding, and is further preferably more deterministic in choosing the correct signal component, thereby avoiding detection errors.

In a first aspect of the present invention, a device for extracting physiological information from remotely detected electromagnetic radiation emitted or reflected by a subject is provided, comprising:
- an interface for receiving a data stream derived from detected electromagnetic radiation, the data stream comprising at least one sequence of signal samples representing a region of interest exhibiting a continuous or discrete characteristic signal including physiological information indicative of at least one at least partially periodic vital signal, and being comprised of at least two wavelength components,
- a transforming unit configured for determining and providing at least one coefficient component suitable for deriving at least one signal component from the at least two wavelength components of the at least one sequence of signal samples,
- a coefficient selection unit for selecting one coefficient component, and
- a signal component unit for providing a signal component based on the selected coefficient component and the at least one sequence of signal samples,
- preferably further comprising:
- a signal processing unit for providing the desired physiological information from the signal component.

The term "wavelength component" as used within the context of present invention is to be understood as being a component of the at least one sequence of signal samples representative for a certain wavelength or wavelength range. Common non-limiting examples are the three wavelength components in RGB signals. However, any other format of signals may be chosen that comprises at least two wavelength components.

The term "signal component" as used within the context of the present invention is to be understood as being a sequence of signal samples which is based on and further a component of the at least one sequence of signal samples of the data stream received by the interface, in the following also input sequence of signal samples. Exemplary ways of providing these "signal component" may be by use of weighing coefficients or coefficient vectors applied to the input sequence of signal samples. These coefficient components may be based on the input sequence of signal samples itself and can, for example, be provided by Blind Source Separation (BSS) methods. These BSS methods encompass Independent Component Analysis (ICA) or Principle Component Analysis (PCA), by way of example.

The term "coefficient component" as used within the context of the present invention is to be understood as a coefficient or coefficient vector that, applied to the input sequence of signal samples, provides a corresponding signal component. Such a "coefficient component" may be provided as a set of coefficient components by methods like the exemplary mentioned BSS methods, and is therein further used to provide the desired signal components. However, within the scope of the present invention, such a coefficient component may also be determined as a single coefficient (vector) instead of automatically providing a set of coefficient components, as it is the case in the established BSS methods, for example.

Although mentioned individually before, the transforming unit and the coefficient selection unit may as well be realized as a single (combined) unit.

In a further aspect of the present invention, a method for extracting physiological information from remotely detected electromagnetic radiation emitted or reflected by a subject is provided, comprising the steps of:
- receiving a data stream derived from detected electromagnetic radiation, the data stream comprising a sequence of signal samples representing a region of interest exhibiting a continuous or discrete characteristic signal including physiological information indicative of at least one at least partially periodic vital signal, and being comprised of at least two wavelength components,
- determining and providing at least one coefficient component from the at least two wavelength components,
- selecting one coefficient component, and
- providing a signal component based on the selected coefficient component and the sequence of signal samples,
- further preferably comprising the step of:
- providing the physiological information based on the signal component.

Regarding the coefficient selection unit, or the step of selecting one coefficient component, it goes without saying that in the case of only one present coefficient component the aforementioned unit or step is automatically realized since the only one coefficient component would automatically be selected due to the lack of choices. However, the coefficient selection unit may be responsible for evaluating this one coefficient component regarding its usability.

With providing the signal component, which can be used for achieving the desired physiological information, like the desired vital signs, by selecting the according coefficient component, the overall process of providing the physiological information gets more efficient. This is due to minimizing the necessary calculations. Whereas the methods according to the above mentioned US 2011/0251493 A1 require the provision of at least two, for example three, (complete) signal components for making a selection, the present invention moves the step of selection to the process of identifying the coefficient component(s). With respect to the method described in US 2011/0251493 A1 the selection would be moved into the BSS steps, thereby avoiding the time and computational power demanding steps of calculating even the unnecessary signal components.

As will also be described later on, this further allows, that not even all possible coefficient components have to be calculated, which makes the method even more efficient and further avoids wasting computational resources.

Preferred embodiments of the invention are defined in the dependent claims. It should be understood that the claimed methods and the claimed computer program can have similar preferred embodiments as the claimed device and as defined in the dependent device claims.

In an embodiment of the device according to the present invention, the coefficient selection unit is further configured for evaluating the at least one coefficient component based on a fixed and predetermined reference vector.

In an embodiment of the method according to the present invention, the method further comprises an evaluation of the at least one coefficient component based on a fixed and predetermined reference vector.

By using a fixed and predetermined reference vector the choice of the coefficient component and thereby the provision of the according signal component containing the desired vital sign data, for example, may be done reliably even though other periodic signal components may result in the end. Further, with a selection based on an evaluation of the coefficient component(s), time and resource demanding computations and calculations, like Fourier-transformation with the signal components, may be avoided. This speeds up the overall provision of the desired data, that is to say is more instantly and does require shorter detection periods, preferably in the range of just a few seconds. The overall result is a deterministic rather than a heuristic approach.

The predetermined vector can be a general predetermined vector for every subject, but can also be chosen individually, for example, after an initial calibration.

In another embodiment of the device according to the present invention, the transforming unit is further configured for determining and providing one coefficient component and the coefficient selection unit is further configured such that the coefficient component provided by the transforming unit is evaluated with respect to the fixed and predetermined reference vector, wherein the transforming unit is preferably further configured such that the determined and provided coefficient component is the coefficient component that results in the signal component with the highest variance.

In another embodiment of the method according to the present invention, one coefficient component is determined and provided and further evaluated with respect to the fixed and predetermined reference vector, wherein the determined and provided coefficient component is preferably the coefficient component that results in the signal component with the highest variance.

The determination of just one coefficient component, at least in a first instance, reduces the general necessary computational steps to a minimum and therefore increases the efficiency of the device and method according to the present invention. The provided coefficient component may then be evaluated, that is to say checked for its usability in providing a signal component that comprises the desired information of physiological data. Assuming that the physiological data provides the most significant and persistent contribution to the changes in the received input sequence of signal samples, the signal component with the highest variance contains the desired physiological information. Accordingly, at first determining and providing the coefficient component resulting in the signal component with the highest variance will suffice for achieving the desired physiological information in most cases, and therefore increase the efficiency since determining and providing the remaining coefficient components may be omitted.

By way of example, and analogue to the mentioned BSS methods, this may be realized by determining the eigenvalues of the covariance matrix of the input sequence of signal samples and determining/providing the eigenvector, which corresponds to the coefficient component, with the highest eigenvalue.

In another embodiment of the device according to the present invention, the coefficient selection unit is designed such that the evaluation is based on the angle between the provided coefficient component and the reference vector and further such that the coefficient component is selected if the angle is less than 45°.

In another embodiment of the method according to the present invention, the step of evaluating the one coefficient component comprises the steps of:
  determining the angle between the coefficient component and the fixed predetermined reference vector, and
  selecting the coefficient component if the absolute value of the angle to the fixed predetermined reference vector is less than 45°.

Assuming that all coefficient components or coefficient component vectors that may be derived by the present method are independent with respect to each other, that is to say orthogonal, this criterion may be used for evaluating the usability of the determined coefficient component. If the angle to the predetermined fixed reference vector is less than 45°, no other coefficient component can exist that will have a smaller angle with respect to the reference vector—due to the orthogonality of the coefficient components with respect to each other. On the other hand, if the angle is 45° or more, at least another, possibly better, coefficient component exists and at least the next coefficient component needs to be determined. This may preferably be the coefficient component that results in the signal component with the next highest variance. Referring to the above mentioned example, this would be the eigenvector with the next highest eigenvalue, for example.

In another embodiment of the device according to the present invention, the transforming unit is further configured for determining and providing at least two coefficient components and the coefficient selection unit is further configured for selecting one of the at least two coefficient components by evaluating the coefficient components.

In another embodiment of the method according to the present invention, at least two coefficient components are determined and provided and one of the at least two coefficient components is selected by evaluating the coefficient components.

Preferably, all the embodiments regarding the evaluation of the coefficient components, wherein each coefficient component comprises a set of elements, thereby forming a corresponding coefficient component vector, comprise a transforming and/or coefficient selection unit or, accordingly, a method step wherein the overall coefficient component (vector) is multiplied by the sign of one of its elements. This element is preferably the element that corresponds to the wavelength component which is influenced the most by the (periodical) vital sign, or physiological information in general. The reason for this is that the element of the coefficient component vector corresponding to the wavelength component which is influenced the most typically gives the highest weight with respect to the other elements to the aforementioned wavelength component. On the other hand, wavelength components with a smaller pulse amplitude may get a small element of the coefficient component vector, such that the sign becomes erratic because the values are close to zero. In the exemplary case, where the data stream comprises RGB color data, the coefficient component vector is multiplied by the sign of the second element which corresponds to the green channel. Alternatively, in an exemplary set-up using IR wavelength components, like for example 750 nm, 880 nm and 980 nm, the strongest pulse influence can be found in the 880 nm wavelength component. Therefore, in this example, the element of the coefficient component vector corresponding to 880 nm is chosen for the aforementioned sign multiplication.

This measure leads to coefficient components or coefficient component vectors that comprise identical signs in order to being comparable with each other and further leading to signal components having always the same sign (i.e. relation with the underlying vital sign). This sign may otherwise be arbitrary since most methods for finding the coefficient components are directed to finding a set of coefficient components that are independent with respect to each other. This, however, is independent of the sign and may therefore not be controlled in each case in a practical realization of the device and/or method according to the present invention.

In another embodiment of the device according to the present invention, the coefficient selection unit is designed such that the evaluation is based on the distance between the coordinates derived from the normalized vectors of the respective coefficient components and the coordinates of the reference vector, and the selection is based on the shortest distance.

In another embodiment of the method according to the present invention, the step of evaluating the at least two coefficient components comprises the steps of:
  determining the distances between the coordinates derived from the normalized vectors of the respective coefficient components and the coordinates of the fixed predetermined reference vector, and
  selecting the coefficient component with the smallest distance.

This way the difference between the coefficient components and the predetermined reference vector, which is preferably normalized as well, can be determined based on the Euclidean distance of the coordinates of the vectors. The minimum of all the determined distances indicates the coefficient component closest to the predetermined reference vector, i.e. closest in its orientation. This embodiment, as well as the following one, can be used in connection with several blind source separation methods, like PCA or ICA. In ICA the resulting independent components are not necessarily orthogonal, and it is therefore not possible to use the aforementioned embodiment with the criterion of comprising an angle less than 45° for a selection. In this (and the following) embodiment all vectors are compared with the reference vector to see which one is best (in terms of distance or angle).

This embodiment encompasses preferably the aforementioned step of multiplying the coefficient components with the sign of one of their elements.

In another embodiment of the device according to the present invention, the coefficient selection unit is designed such that the evaluation is based on the angle between the provided at least two coefficient components and the reference vector and further such that the coefficient component with the smallest angle is selected.

In another embodiment of the method according to the present invention, the step of evaluating the at least two coefficient components comprises the steps of:
  determining the angle between the respective coefficient components and the fixed predetermined reference vector, and
  selecting the coefficient component with the smallest angle to the fixed predetermined reference vector.

This way, the respective angles between the coefficient component vectors and the predetermined reference vector are determined. The minimum of the determined angles indicates the coefficient component closest to the predetermined reference vector, i.e. closest in its orientation. Thereby, a normalization of the coefficient component is not necessary, but might be done anyway.

This embodiment encompasses preferably the aforementioned step of multiplying the coefficient components with the sign of one of their elements.

In another embodiment of the device of the present invention, the predetermined reference vector is based on the skin tone of the subject.

The light reflected by the subject (and detected by the device) consists basically of two components: one diffuse reflection component with light which has travelled through the skin and shows its color including variations thereof due to the physiological manifestations of the vital sign to be detected, e.g. the pulse, and one component of directly reflected light which shows the color of the light source, also known as the specular reflection. Whereas the latter may vary depending on the reflection angle and (the color of) the light source, but not on the alterations based on the vital sign to be detected, the first diffuse reflection component is substantially independent of the angle. Since this component alters around the color of the skin, or the skin tone, a search for a signal component close to a value depending on this skin tone aids in disregarding the signal components based on specular reflection. In the consequence, a corresponding reference vector can be provided for evaluating the coefficient components based on this skin tone.

As a basis, the skin tone may be chosen for every subject individually. Also, it is possible, and also preferred within the context of the present invention, to determine and use a "standardized" skin tone. Such a "standardized" skin tone may be determined in an empirical approach by determining the skin tones of a representative amount of subjects and calculating the average, for example. The ("standardized") skin tone may then be the basis in an approach for determining the fixed predetermined vector according to the present invention.

In another embodiment of the device of the present invention, the interface is designed to receive RGB color data and the fixed vector is close to [−0.4, 0.8, −0.4], preferably close to [−0.41, 0.82, −0.41], more preferably close to [−0.408, 0.817, −0.408], and even more preferably close to [−0.4082, 0.8165, −0.4082].

The term "close to" as used within the context of the present invention, especially within the context of the aforementioned vectors, is to be understood as encompassing all the values, e.g. vector elements for a vector, that fall under the given values considering their respective accuracy which is intended to allow a deviation of ±1 in the respective last digit. For example, 0.8 is to be understood as encompassing the values from 0.7 to 0.9, −0.82 is to be understood as encompassing the values from −0.81 to −0.83, and so on.

The inventors found that in a set-up where the interface is able to receive and further provide the data in the RGB format, like but not limiting to digital cameras and camcorders, webcams etc., the subject is a human being and the vital sign to be detected is the pulse (HB), the latter could be determined by the equation (1):

$$HB \approx 1.5 R_n - 3 G_n + 1.5 B_n \qquad (1),$$

with $R_n$, $G_n$ and $B_n$ being the elements of the RGB data, achieved by dividing the individual value by the mean (over a time-interval) value of the respective channel. This means that these RGB elements mostly just slightly deviate from the average or mean value, i.e. the skin tone of the individual. This deviation includes the HB information. With the weighing by the factors 1.5, −3 and 1.5 the effect of changes due to motion are substantially eliminated, since motion typically modulates the RGB data to the same percentage, and a direct correspondence between RGB data and HB can be provided. Further, using these factors as a basis a fixed predetermined vector may be found close to which a weighing vector, that is to say a weighing coefficient component vector, is oriented.

The inventors further found that this is also true for a signal component comprising the HB signal which may also be derived by BSS as mentioned before. Accordingly, the selection of the signal component containing the desired HB signal information, for example, can be directed to finding the corresponding coefficient component vector closest to the predetermined vector. Normalization of the vector [1.5, −3, 1.5] leads to [0.4082, −0.8165, 0.4082] and further multiplication by the sign of the second element leads to the most preferred reference vector [−0.4082, 0.8165, −0.4082].

Aside from this embodiment using RGB color data, in another embodiment of the device of the present invention, the interface is designed to receive multi-wavelength infrared data and the fixed vector is close to [−0.3, −0.8, −0.5], preferably close to [−0.26, −0.80, −0.54]. This is preferably applicable for wavelength ranges of 750 nm to 1000 nm. When, for example, wavelengths close to 780 nm, 880 nm and 980 nm are chosen, again the second component, i.e. corresponding to 880 nm is primarily affected by the physiological information to be detected. Accordingly, the way of choosing a coefficient component may be such that the second element of the coefficient component vector is relatively high.

In another embodiment of the device according to the present invention, the coefficient components are realized as vectors having at least two elements and the coefficient selection unit is further designed such that the evaluation of the coefficient components is realized by comparing a relative value of a chosen element of a respective coefficient component vector with the relative values of the same element of the other coefficient component vectors and further such that the selection of the coefficient component vector is based on the highest relative value of the chosen element, wherein the interface is preferably designed to receive RGB color data and the chosen element corresponds to the green channel. In the alternative embodiment using IR wavelength components with 750 nm, 880 nm and 980 nm the chosen element corresponds to the middle channel with 880 nm.

In another embodiment of the method according to the present invention, the coefficient components are realized as vectors having at least two elements and the step of evaluating the at least two coefficient component comprises the steps of:
   determining a relative value of a chosen element of each coefficient component vector, and
   selecting the coefficient component with the highest relative value, wherein the data stream is preferably comprised of RGB color data and the chosen element corresponds to the green channel. Again, in IR the chosen element corresponds to 880 nm, considering the wavelength components as mentioned before.

In this embodiment the coefficient component is chosen by finding the one that comprises the highest relative value in one chosen element of the coefficient component vectors, wherein this element is preferably characterized as being the one corresponding to the wavelength component that is mostly affected by the physiological information, i.e. the detected (periodical) vital sign. In the mentioned exemplary case of RGB color data this wavelength component is the green channel. In the other exemplary case of the mentioned IR wavelength components, the wavelength component is the one corresponding to 880 nm. Accordingly, the selection of the coefficient component vector is such that the one is chosen that gives the highest weight to this second wavelength component, i.e. green or 880 nm, when calculating the respective signal component.

This embodiment, as well as the aforementioned embodiments wherein the evaluation is realized with respect to a reference vector, can be used in connection with several blind source separation methods, like PCA or ICA.

In an exemplary embodiment, assuming three dimensional coefficient component vectors, this can be done by calculating the difference between the second element of the coefficient component vector and the absolute value of the sum of all elements of this vector. By comparing these differences calculated for all determined coefficient component vectors the one comprising the highest value is chosen for calculating and thereby providing the desired signal component, e.g. by multiplying the chosen coefficient component with the input sequence of signal samples.

This embodiment encompasses preferably the aforementioned step of multiplying the coefficient components with the sign of one of their elements.

In yet another aspect of the present invention, there is provided a computer program which comprises program code means for causing a computer to perform the steps of the method according to the present invention when said computer program is carried out on a computer.

As used herein, the term "computer" stands for a large variety of processing devices. In other words, also mobile devices having a considerable computing capacity can be referred to as computing device, even though they provide less processing power resources than standard desktop computers. Furthermore, the term "computer" may also refer to a distributed computing device which may involve or make use of computing capacity provided in a cloud environment.

In other possible embodiments of the device of the present invention, the data stream comprises a plurality of sequences of signal samples, each representing an individual region of interest on the subject and each being handled by the transforming unit, the coefficient selection unit and the signal component unit of the device individually. By monitoring a plurality of regions of interest a combination of the detected signals can be calculated. Thereby, erroneous readings or partial changes in one of the monitored regions of interest due to interferences may be easily disregarded or do not influence the overall detected data in a significant way.

In another possible embodiment of the device of the present invention, the device is further designed to track the individual regions on the subject over time. This allows the device of the present invention being used in a set-up where the subject moves with respect to the device. This is especially advantageous in remote photoplethysmography (R-PPG), where no direct contact of the device and the subject exists.

In another possible embodiment of the device of the present invention, the device further comprises a data combining unit configured for generating an enhanced selected signal component by combining the individual selected signal components for the individual regions. This combining unit will then be able to combine the individual signal components based on the aforementioned plurality of sequences of signal samples and is thereby able to provide the aforementioned combination of detected signals. Thereby, undesired interferences or other errors in the detected signals may me either lost by the combination of the detected signals or may even be detected in a separate comparison step and then be disregarded.

BRIEF DESCRIPTION OF THE DRAWINGS

These and other aspects of the invention will be apparent from and elucidated with reference to the embodiments described hereinafter. In the following drawings.

DETAILED DESCRIPTION OF THE INVENTION

The following section describes exemplary approaches to remote photoplethysmography utilizing several aspects of the device and method of the invention. It should be understood that single steps and features of the shown approaches can be extracted from the context of the respective overall approach or embodiments. These steps and features can therefore be part of separate embodiments still covered by the scope of the invention.

Basic approaches to remote photoplethysmography are described in Verkruysse, W. et al. (2008), "Remote Plethysmographic Imaging Using Ambient Light" in Optics Express, Optical Society of America, Washington, D.C., USA, Vol. 16, number 26, pp. 21434-21445.

Figure 1:
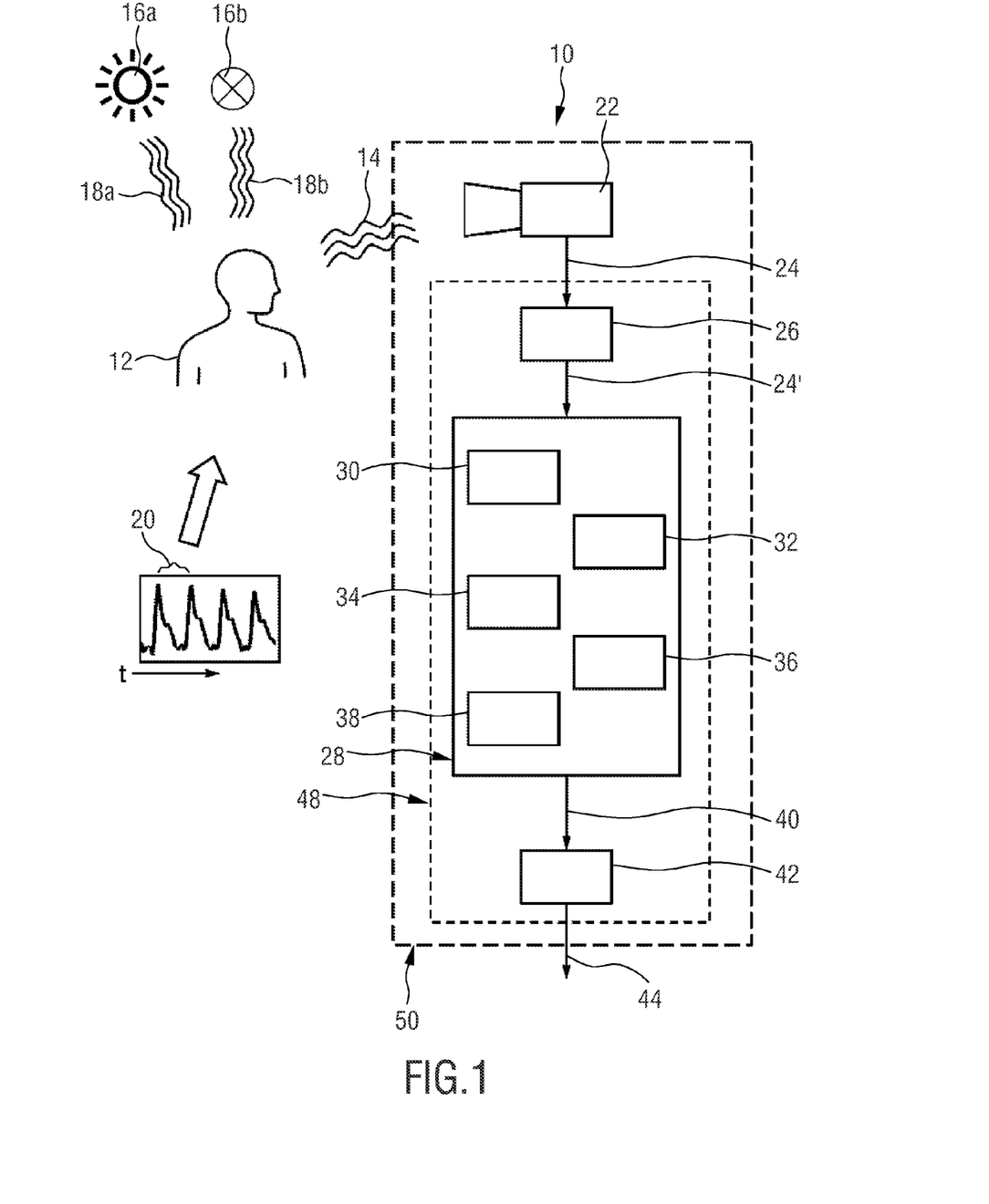
FIG. 1 shows a schematic illustration of a general layout of a device in which the present invention can be used.

FIG. 1 shows a schematic illustration of a device for extracting physiological information which is denoted by a reference numeral 10. For instance, the device can be utilized for recording image frames representing a remote subject 12 for remote PPG monitoring. The image frames can be derived from electromagnetic radiation 14 reflected by the subject 12. Possibly, under certain conditions, in particular specific luminance conditions, at least part of the electromagnetic radiation 14 could be emitted or transmitted by the subject 12. Radiation transmission may occur when the subject 12 is exposed to strong illumination sources shining through the subject 12. Radiation emission may occur when infrared radiation caused by body heat is addressed and captured. However, for remote PPG applications, a huge portion of the electromagnetic radiation 14 can be considered radiation reflected by the subject 12. The subject 12 can be a human being or an animal, or, in general, a living being. Furthermore, the subject 12 can be part of a human being highly indicative of a desired signal, e.g., a face portion or, in general, a skin portion.

A source of radiation, such as sunlight 16a or an artificial radiation source 16b, also a combination of several radiation sources can affect or impinge on the subject 12. The radiation source 16a, 16b basically emits incident radiation 18a, 18b striking the subject 12. For extracting physiological information from the recorded data, e.g., a sequence of image frames, a defined part or portion of the subject 12 can be detected by a sensor means 22. The sensor means 22 can be embodied, by way of example, by a camera adapted for capturing information belonging to at least one spectral component of the electromagnetic radiation 14. Needless to say, the device 10 also can be adapted to process input signals, namely an input data stream, already recorded in advance and, in the meantime, stored or buffered. As indicated above, the electromagnetic radiation 14 can contain a continuous or discrete characteristic signal which can be highly indicative of at least one at least partially periodic vital signal 20. The characteristic signal can be embedded in an (input) data stream 24.

According to an embodiment, for data capturing, a potentially highly indicative portion of the subject 12 can be selected (or: masked with a pixel pattern). When agglomerating respective single pixel values of the pixel pattern at an instant, a mean pixel value can be derived from the pixel pattern. In this way, the detected signals can be normalized and compensated for overall disturbances to some extent. Generally, the characteristic signal is considered to contain a constant (DC) portion and an alternating (AC) portion superimposing the DC portion. Applying signal processing measures, the AC portion can be extracted and, furthermore, compensated for disturbances. For instance, the AC portion of the characteristic signal can comprise a dominant frequency which can be highly indicative of the subject's 12 heart rate. The mean pixel value can be represented by a characteristic signal. The vital signal of interest 20 can be embedded in slight fluctuations (slight periodic property changes) of the characteristic signal. In the following, the captured data stream can be considered a representation of a certain area of interest in the subject 12 which may cover an agglomerated pixel area covering a plurality of pixels. In FIG. 1, the vital signal 20 may allow several conclusions concerning heart rate, heartbeat, heart rate variability, respiratory rate, or even oxygen saturation.

The known methods for obtaining such vital signals may comprise tactile heart rate monitoring, electrocardiography, or pulse oximetry. To this end, however, obtrusive monitoring was required. As indicated above, an alternate approach is directed to unobtrusive remote measuring utilizing image processing methods.

The data stream 24 comprising the continuous or discrete characteristic signal can be delivered from the sensor means 22 to an interface 26. Needless to say, also a buffer means could be interposed between the sensor means 22 and the interface 26. Downstream of the interface 26, the input data stream 24' can be delivered to a processing module or processing unit 28. The processing unit 28 can be considered a computing device or, at least, part of a computing device driven by respective logic commands (program code), so as to provide for desired data processing. The processing unit 28 may comprise several components or units which are addressed in the following. It should be understood that each component or unit of the processing unit 28 can be implemented virtually or discretely. For instance, the processing unit 28 may comprise a number of processors, such as multi-core processors or single-core processors. At least one processor can be utilized by the processing unit 28. Each of the processors can be configured as a standard processor (e.g., central processing unit) or as a special purpose processor (e.g., graphics processor). Hence, the processing unit 28 can be suitably operated so as to distribute several tasks of data processing to adequate processors.

In accordance with an embodiment of the present invention, the processing unit 28 comprises a segmentation unit 30 configured for determining an indicative frame section, in particular a skin portion of the subject 12, such that the indicative frame section preferably comprises the region of interest. It should be mentioned that both the indicative frame section and the region of interest can match or correspond to each other. However, alternatively, the indicative frame section and the region of interest also may somehow deviate in size or position. The segmentation unit 30 can be adapted for skin segmentation and/or feature tracking measures. Both skin segmentation and feature tracking can be utilized for pattern detection, so as to initially detect the region of interest and to track the region of interest over time. Hence, the segmentation unit 30 can contribute in motion compensation.

In an alternative embodiment, however, pattern detection or skin segmentation can be performed manually by a user of the device 10. For instance, the user can mask a face portion or a skin portion of the subject 12 in a frame representing an initial frame for determining an initial frame section to be processed.

The processing unit 28 may further comprise a partitioning unit 32 configured for selectively partitioning the region of interest into at least two defined signal subsets. In this way, a sequence of frames embedded in the data stream can be split into at least two sub-sequences. As used herein, splitting or partitioning typically refers to dividing an area in a region of interest.

The processing unit 28 may further comprise a signal extraction unit 34 for processing each of a plurality of the at least two distinct sub-sequences generated by the partitioning unit 32. In this way, a plurality of distinct indicative characteristic sub-signals can be derived. So, instead of processing the region of interest as a whole, sub-portions thereof can be processed separately. In this way, locally occurring disturbances and distortions can be addressed. Signal processing, in particular signal extraction, can be performed by a signal extraction unit 34. The signal extraction unit 34 can be configured for processing each of a plurality of the at least two distinct sub-sequences. In other words, the signal extraction unit 34 does not necessarily have to process every sub-sequence generated by the partitioning unit 32.

Given that the portion of interest can be locally corrupted by distortions, it can be assumed that some of the at least two distinct sub-sequences (of respective subsets) exhibit heavily distorted signals while others may exhibit far less distorted signals. The higher the number of signal subsets the region of interest is partitioned into, the better a present distortion occurrence can be "matched" by some of the subsets.

As mentioned above, preferably, the partitioning unit 32 and the signal extraction unit 34 can be further configured for multiply partitioning and processing the region of interest such that at least two groups of signal subsets are formed and processed accordingly. In this way, each time instant (frame number) of the region of interest can be processed several times. The provision of at least two groups of defined signal subsets allows for far more flexibility when facing locally occurring distortions and disturbances in the region of interest.

In addition, the processing unit 28 can comprise a data combining unit 36 configured for generating an enhanced characteristic signal under consideration of the extracted characteristic sub-signals. For generating the enhanced characteristic signal, particularities of the characteristic sub-signals can be considered. For instance, statistical measures can be applied so as to attenuate outliers which are supposed to be mainly caused by locally occurring disturbances. Hence, the resulting enhanced characteristic signal can be further improved. It should be noted that on a basis of the characteristic sub-signals, local disturbance-related artefacts can be precisely realized and addressed. By contrast, when processing the region of interest as a whole, merely rather untargeted (in terms of local distortions) signal enhancement measures can be applied.

Still, however, the processing unit 28 can further comprise a signal enhancement unit 38 which is configured for further processing the characteristic signal generated by the signal combining unit 36. For instance, the signal enhancement unit 38 can be configured to seek for dominant frequencies in the characteristic signal. Alternatively, the signal enhancement unit 38 can be configured for filtering the characteristic signal such that frequency portions which are considered not to be indicative of the desired vital signal 20 can be disregarded or, at least, attenuated.

Eventually, a processed data stream 40 can be generated by the processing unit 28. Downstream of the processing unit 28, an (output) interface 42 can be provided to which the processed data 40 can be delivered. Both interfaces 26, 42 can be embodied by the same (hardware) connectors. Via the interface 42, output data 44 can be made available for further analyses and/or for display measures. The processing unit 28 as well as the interfaces 26, 42 can be embodied in a common processing apparatus or housing 48. Reference numeral 48 can also describe a virtual system boundary. Still, also the sensor means 22 can be integrated in the common processing housing 48. A potential overall system boundary of the device 10 is denoted by a reference numeral 50. It should be understood that the device 10 also can be implemented as a distributed device. For instance, at least the sensor means 22 can be partitioned separate or distant from the processing unit 28. Moreover, functional entities of the processing unit 28 can be implemented in distributed processing devices which can be connected via cable or wireless connections or networks.

Figure 2A:
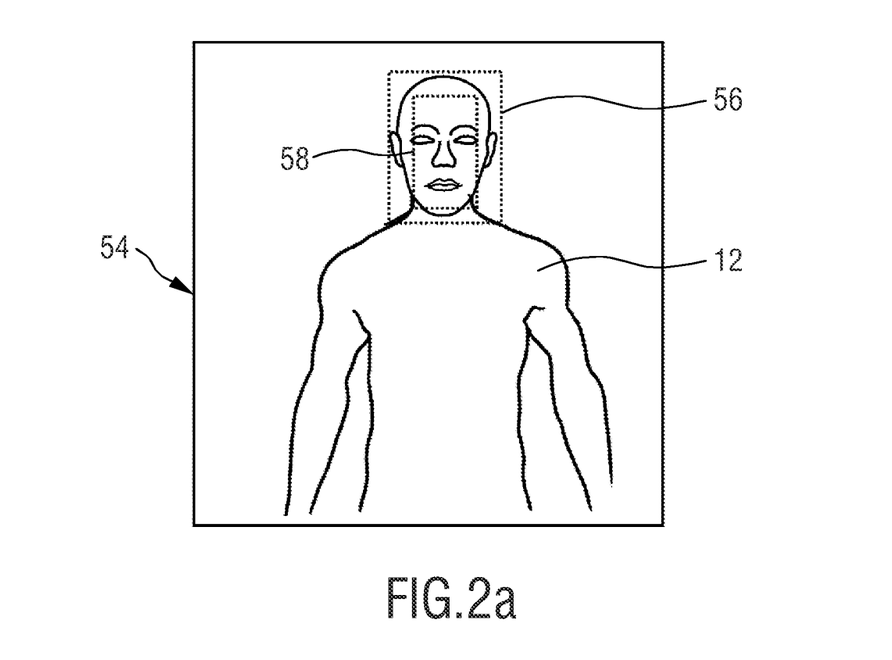
FIG. 2a shows a simplified exemplary frame representing an observed subject.

FIG. 2a illustrates an (image) frame 54 comprising a representation of the subject 12. As mentioned above, a skin portion of the subject 12, in particular a face portion of the subject 12, is considered to be highly indicative of the desired vital signals. By way of example, in the frame 54 an indicative frame section 56 is chosen. To this end, pattern detection or recognition can be applied. For instance, the indicative frame section 56 can be determined upon face detection. Typically, the indicative frame section 56 comprises or corresponds to a region of interest 58. In FIG. 2a, exemplarily, the indicative frame section 56 and the region of interest 58 do not match.

As used herein, the term "region of interest" typically refers to a set or an array of pixels. Since motion-related disturbances have to be expected for remote photoplethysmography, it should be understood that the precise position of the region of interest 58 in each frame 54 of a series (sequence) of frames 54 can drift or move over time. Therefore, preferably, motion compensation measures are applied, so as to ensure that the region of interest 58 can be tracked over time.

Figure 2B:
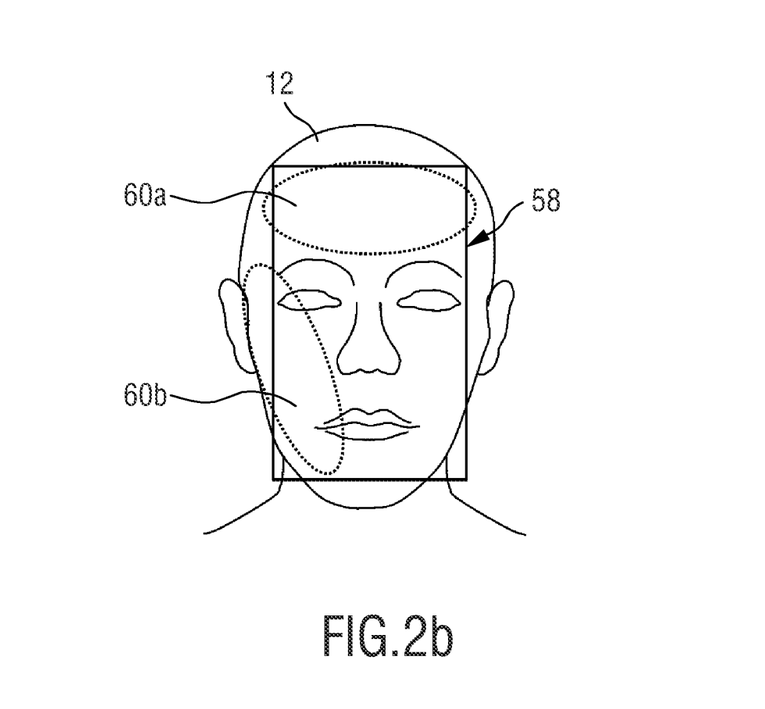
FIG. 2b shows an enlarged partial view of the frame according to FIG. 2a, representing a region of interest.

FIG. 2b is an enlarged view of the region of interest 58 in the subject 12 chosen in FIG. 2a. As mentioned above, the region of interest 58 can be locally corrupted by distortions. For instance, distorted regions 60a, 60b can be present in the region of interest 58. In some subjects 12, depending on the observing environment, the forehead region can be susceptible to specular reflections. This applies in particular when the forehead region is sweaty or greasy. Therefore, the distorted region 60a can adversely influence the results of data processing focusing on the region of interest 58 as a whole. Basically, the same may apply to the distorted region 60b.

Specular reflection is a part of the electromagnetic radiation 14 reflected by the subject 12 in the regions of interest 58. The reflected electromagnetic radiation 14 can therefore be regarded as comprising this specular reflection part and a diffuse reflection part. The diffuse reflection results from the radiation 18a, 18b, e.g. light, getting into or passing through the subject's skin and being emitted with a component of the skin tone and being further influenced by the desired vital sign 20, at least indirectly. Accordingly, the diffuse reflected part of the reflected electromagnetic radiation 14 is relevant for determining the desired vital sign 20, whereas the specular reflection part is merely influenced by the radiation source 16a, 16b, e.g. its type and the wavelength of the emitted radiation 18a, 18b, and the angle of the region of interest 58 of the subject 12 with respect to the radiation source 16a, 16b.

Finding the separate signal components influencing the overall reflected radiation can be achieved by a blind source separation (BSS) approach, for example. One example for such an approach is Independent Component Analysis (ICA), like for example described by M. Z. Poh, D. J. McDuff, and R. W. Picard, in "*Non-contact, automated cardiac pulse measurements using video imaging and blind source separation*", Opt. Express. 2010, Vol. 18 (10), pp. 10762-10774, which is herein fully incorporated by reference. Another example for such an approach is Principle Component Analysis (PCA), like for example described by M. Lewandowska, J. Ruminski, T. Kocejko, and J. Nowak, in "*Measuring Pulse Rate with a Webcam—a Non-contact Method for Evaluating Cardiac Activity*", Proc. FedCSIS, 2011, pp. 405-410, which is herein fully incorporated by reference.

Figure 3:
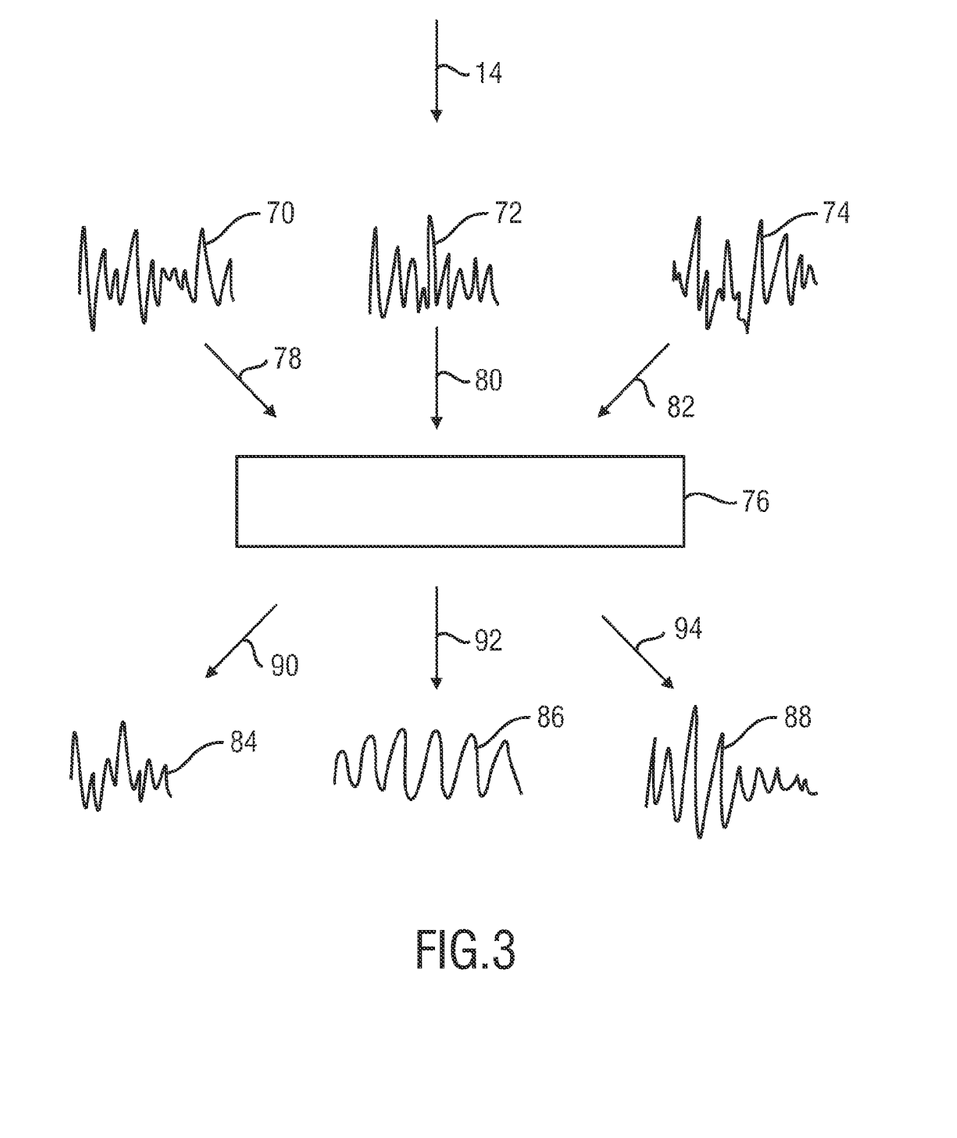
FIG. 3 shows an exemplary embodiment of BSS via ICA.

Both methods provide a set of signal components derived from the originally received wavelength components of the electromagnetic radiation 14. This is exemplary illustrated in FIG. 3 for the electromagnetic radiation 14 being detected as an RGB-signal with the three wavelength components 70, 72 and 74, representing the Red, Green and Blue channel. These wavelength components 70, 72 and 74 are submitted to an ICA step 76 as illustrated by arrows 78, 80 and 82. The results are in this example three signal components 84, 86 and 88. This is illustrated by arrows 90, 92 and 94. In the aforementioned ICA approach, which is also described in US 2011/0251493 A1, the selection of the signal component comprising the information about the desired vital sign 20 is effected by finding the signal component with a periodic signal. This relies on the assumption that only one periodic signal is present.

With both parts of the electromagnetic radiation 14, i.e. the specular reflection and the diffuse reflection, changing over time, and even the specular reflection part being able to change periodically, for example by a periodic movement of the subject of some kind with respect to the radiation source 16a, 16b, a selection based on this assumption is likely to fail.

In the example of RGB components, an elimination of the undesired specular reflection part can be achieved by using color difference signals. For this, two orthogonal color difference signals are build, for example X=R−G and Y=0.5R+0.5G−B. Since the motion of the subject and therefore the change in specular reflection would affect all three channels, whereas the diffuse reflection would affect X and Y differently, equation (2) indicates the pulse (HB)

$$HB = \frac{X_n}{Y_n} - 1, \tag{2}$$

wherein $X_n$ and $Y_n$ represent the respective normalized values.

Further, a "standardized" skin tone can be used as a basis, wherein this skin tone is [R, G, B]=[0.7682, 0.5121, 0.3841]. Based on this "standardized" skin tone, which was found by the inventors testing 117 people having different skin tones, deviations from the skin tone of a respective subject can be transformed to a "standardized" skin tone deviation by equations (3)

$$R_S=0.7682R_n, G_S=0.5121G_n, B_S=0.3841B_n \tag{3}$$

wherein $R_n$, $G_n$ and $B_n$ are the respective detected RGB values divided by their mean values. This $R_S$, $G_S$ and $B_S$ are independent of the radiation source 16a, 16b, e.g. its color, and provide the skin tone of a respective subject regardless of the color of the radiation source 16a, 16b.

An according HB value can be achieved by $X_S$ and $Y_S$ as shown in equations (4) and (5)

$$X_S = \frac{R_S - G_S}{0.7682 - 0.5121}, \tag{4}$$

$$Y_S = \frac{R_S + G_S - 2B_S}{0.7682 + 0.5121 - 0.7682}, \tag{5}$$

The HB is then given by equation (6)

$$HB = \frac{X_S}{Y_S} - 1, \tag{6}$$

The respective signal component, which may for example be derived by BSS, e.g. ICA or PCA, as described before can also be regarded as a time dependent deviation from the mean skin tone $R_n B_n G_n$, respectively multiplied with the elements $c_1$, $c_2$ and $c_3$ of a coefficient component vector. The HB can be determined from this according to equation (7)

$$HB=c_1R_n+c_2G_n+c_3B_n \tag{7}$$

These elements can be derived via ICA or PCA, for example, in which the coefficient component vectors [$c_1$, $c_2$, $c_3$] are determined for providing the respective signal components.

According to the present invention, finding the desired signal component can also be effected by finding the corresponding coefficient component (vector) [$c_1$, $c_2$, $c_3$].

Rewriting equation (6) to equation (8)

$$\log(1 + HB) = \log\left(\frac{X_S}{Y_S}\right) \tag{8}$$
$$= \log(X_S) - \log(Y_S),$$

and assuming for a Taylor expansion of the logarithms that all the arguments of the logarithms are very close to 1, the approximation of equation (9) is achieved as a result $$HB \approx X_S - Y_S \tag{9}$$

With equations (4) and (5) as well as with equations (3), HB can be written as demonstrated in equation (10)

$$HB \approx 1.5R_n - 3G_n + 1.5B_n \tag{10}$$

which gives [$c_1$, $c_2$, $c_3$] as [1.5, −3, 1.5] or normalized as [0.4082, −0.8165, 0.4082].

Since the coefficient component vectors are independent of each other, and since this criterion is not influenced by the sign of the respective vectors, the outcome of the coefficient component vectors might be such that the sign of the vectors may change arbitrarily from case to case, or from time to time if the processing is performed on sequential intervals. This is remedied by a multiplication of the vector with the sign of its second element, which corresponds in the example described here to the green channel. This leads to the reference vector [−0.4082, 0.8165, −0.4082] for RGB data.

In a similar manner, reference vectors for other wavelength components can be determined, like [−0.26, −0.80, −0.54] for the IR wavelength components 750 nm, 880 nm and 980 nm. Accordingly, the following description referring to the mentioned reference vector for RGB data is also valid for other data streams comprising other wavelength components, like but not limiting to the exemplary mentioned IR wavelength components, by adapting the description with respect to the reference vector for said wavelength components.

The reason for using the second channel in the present case is that normally the green wavelength component, that is to say the green channel, is mostly influenced by the physiological information, e.g. vital signs like the pulse. Therefore, keeping the contribution of the green channel with the same sign is desired in order to achieve comparable and usable coefficient components and therefore usable signal components.

Based on this, the choice of the correct and desired signal component may be done in a deterministic approach by choosing the coefficient component (vector) that is closest in its orientation to this reference vector. This can either be done by calculating the Euclidean distance between the endpoints of the (normalized) vectors of the coefficient component vector and the reference vector, or by determining the angle between those vectors. Accordingly, the coefficient component is chosen that shows the lowest (Euclidean) distance or the minimum in the calculated angles.

In the exemplary described device 10 this is realized by providing the device 10 with a transforming unit 96, a coefficient selection unit 98, a signal component unit 99 and a signal processing unit 100.

Figure 4:
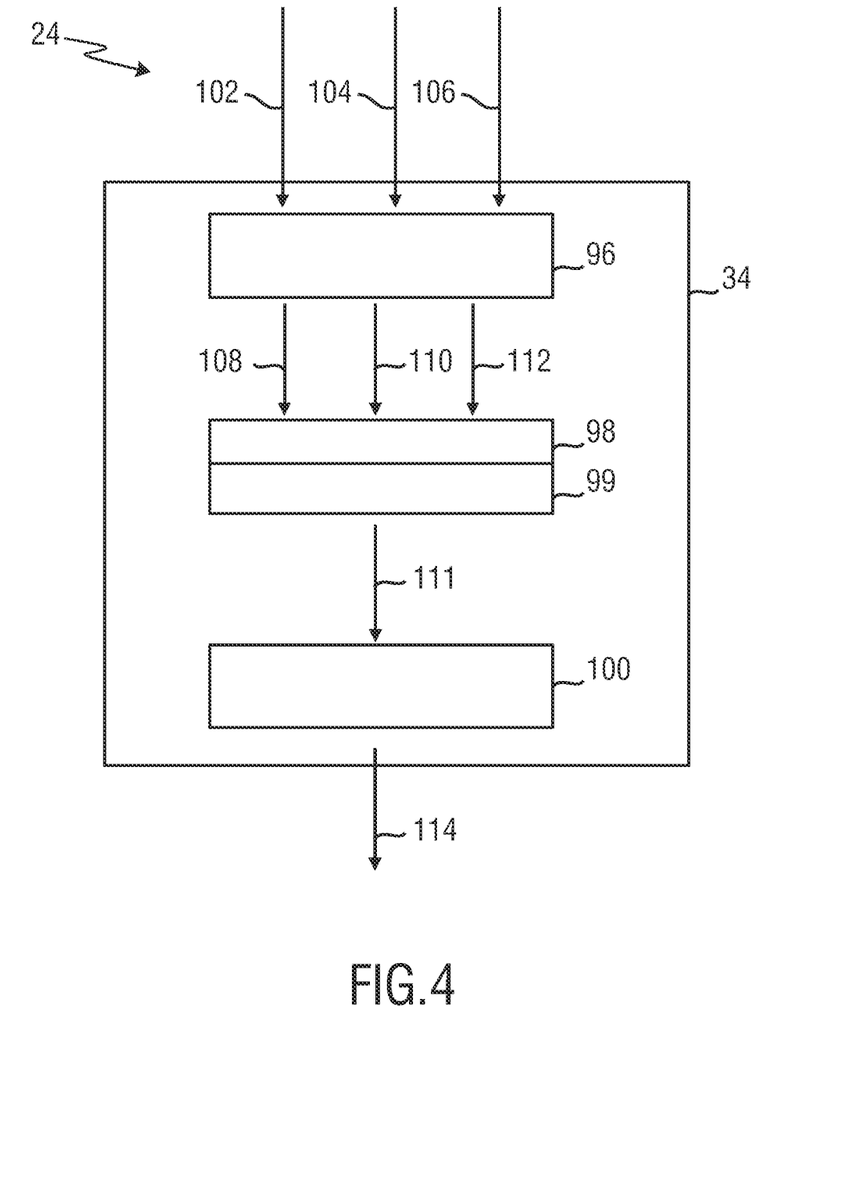
FIG. 4 shows an exemplary embodiment of a part of the device of the present invention.

This is exemplary shown in FIG. 4, wherein these units are considered as parts of the signal extraction unit 34. Therein the transforming unit 96 receives the data stream 24 being comprised of at least two wavelength components. In the present example, wherein the signal stream 24 comprises RGB data, signal 24 has three wavelength components 102, 104 and 106. Each wavelength component resembles one of the three wavelength components of RGB, i.e. red, green or blue. For these wavelength components 102, 104 and 106 three coefficient components 108, 110 and 112 may be calculated in the transforming unit 96. This may, for example, be done similar to methods used and known from BSS approaches. By way of example, the covariance matrix of the input signal characterized by the three wavelength components 102, 104 and 106 may be calculated. From this covariance matrix the eigenvalues and further the eigenvectors may be determined. These eigenvectors then result in the desired coefficient component vectors 108, 110 and 112. For this step, the eigenvectors are preferably multiplied by the sign of the second element of the eigenvector, in this case the element corresponding to the green channel. The coefficient selection unit 98 then analyses the three coefficient components 108, 110 and 112 in order to find the coefficient component that results in the signal component containing the desired information regarding the vital sign 20. This is done by determining which coefficient component is the closest to the predetermined reference vector [−0.4082, 0.8165, −0.4082], preferably according to the methods as explained before. Assuming, in this example, the $2^{nd}$ coefficient component 110 is the closest, coefficient component 110 is provided by the coefficient selection unit 98 to the signal component unit 99. The signal component unit 99 then calculates the desired signal component 111. This is realized by multiplying the input signal, i.e. the wavelength components 102, 104 and 106 with the coefficient component vector 110, that is to say by providing the sum of the wavelength components 102, 104 and 106 each wavelength component weighed by the respective element of the coefficient component vector 110. The resulting signal component 111 is then provided to the signal processing unit 100.

The signal processing unit 100 may then determine and provide the desired vital sign 20 based on the signal component 111. This is illustrated by an arrow 114.

Although, signal processing unit 100 is described in this example as being part of the signal extraction unit 34, it goes without saying that signal processing unit 100 may be a single unit of the device 10 or part of another of the aforementioned units of processing unit 28, for example. Further, it goes without saying that although the device has been described exemplary for a signal stream 24 comprising RGB data, any other data format comprising at least two wavelength components, preferably at least three wavelength components may be used accordingly, providing that the necessary modifications to the predetermined reference vector based on the aforementioned steps for achieving this reference vector are made in accordance to the present invention. The same applies for the method according to the present invention which is as well derivable from the aforementioned description.

In an alternative embodiment according to the present invention, the coefficient component vector may be selected in the coefficient selection unit 98 by comparing the values of a chosen element of the coefficient component vectors. In this exemplary case of RGB color data, the element used for this comparison is again the second element due to its aforementioned significance, i.e. influence of the physiological information in the green, i.e. second, channel. This comparison step is in this embodiment realized by calculating the difference between the second element and the absolute value of the sum over all the elements of the respective vector. This is done for all, in this case all three, coefficient component vectors, and the coefficient component vector having the highest resulting value is chosen.

This approach again uses the characteristic of the physiological information being strongest in the second, i.e. the green channel of the wavelength components.

Figure 5:
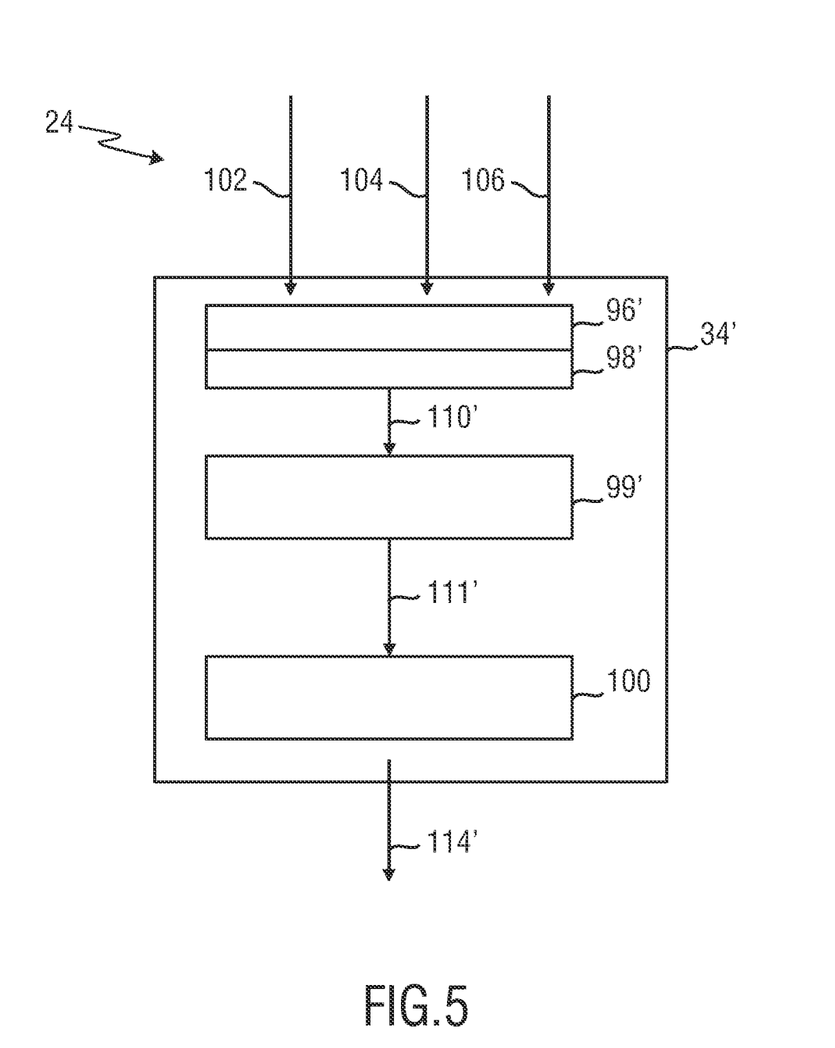
FIG. 5 shows another exemplary embodiment of a part of the device of the present invention.

A second alternative embodiment moves the step of choosing the desired coefficient component to a point before the coefficient components are actually calculated. This is illustrated in FIG. 5, wherein a coefficient selection unit 98' is illustrated as a part of a transforming unit 96'. Since the signal extraction unit 34 in FIG. 4 and the signal extraction unit 34' in FIG. 5 basically comprise identical or similar features, identical parts are designated by the same reference numerals in the following and are not further described. Otherwise, similar parts are designated by the same reference numerals followed by a prime (').

The desired signal component is in most cases the signal component comprising the highest variance. Therefore, in the transforming unit 96' the determination may be realized as mentioned before for the transforming unit 96. However, the step may be stopped at the step of the eigenvalues. The absolute value of the eigenvalues determined in such an approach corresponds to the respective variance of the signal component resulting by multiplication of the resulting coefficient component, in other words the eigenvectors, and the input signal, i.e. the wavelength components. This means the higher the eigenvalue the higher the variance in the overall resulting signal component. As a result, in the present embodiment this is determined in the coefficient selection unit 98' by comparing the eigenvalues, providing the highest eigenvalue, meaning the eigenvalue having the highest absolute value. Further, the coefficient selection unit 98' determines the corresponding eigenvector and in the following, by again multiplying the vector with the sign of the second element of the vector, the coefficient component (vector) 110'.

The coefficient component vector 110' is then provided to the signal component unit 99' for determining and providing the signal component 111'. The following procedure can be regarded identical to the one as described before for the signal extracting unit 34 and results in the desired provision of the vital sign 20 as illustrated by an arrow 114'.

This method and device is beneficial since it is not necessary to calculate all the coefficient components 108, 110 and 112 every time. Hence, computational resources may be saved and a more effective and faster method is provided.

For cases in which the signal component comprising the highest variance is not the desired signal component, a further evaluating step is included. This evaluation step, which is included in the coefficient selection unit 98' for example, may evaluate the achieved coefficient component vector 110'. This can be done in a way analogue to the evaluation methods as described before. For this, the angle between the coefficient component 110' and the aforementioned reference vector [−0.4082, 0.8165, −0.4082] is determined. If this vector is less than 45°, this coefficient component 110' is the coefficient component leading to the desired signal component. This is due to the characteristic of the coefficient components being orthogonal with respect to each other. As a consequence, if one vector comprises an angle less than 45°, no other vector will be able to have a smaller angle with the reference vector.

If, however, the angle of the determined coefficient component is 45° or higher, than in further steps of this method the next highest eigenvalue is preferably chosen and the corresponding eigenvector determined. This leads to the next coefficient component, as described before, and so on.

Due to this case dependent calculation, the necessary time, and therefore the demand in computational resources, is significantly lowered overall, as already mentioned before.

As a further step that is applicable to all the embodiments mentioned before, an optimization of the signal component 111 or 111' provided to the signal processing unit 100, for example, might be done. This optimization is exemplary realized by a so-called overlap-add procedure. Such procedures are exemplary described by Rabiner, Lawrence R.; Gold, Bernard (1975), *Theory and application of digital signal processing*, Englewood Cliffs, N.J.: Prentice-Hall, pp. 63-67 (ISBN 0-13-914101-4); and Oppenheim, Alan V.; Schafer, Ronald W (1975), *Digital signal processing*, Englewood Cliffs, N.J.: Prentice-Hall (ISBN 0-13-214635-5), which are herein fully incorporated by reference.

In such an overlap-add procedure, a certain interval length is chosen. Then, a Hanning window function, or any other suitable window function, is applied to such an interval length of the signal component 111, 111'. Half an interval length later, another interval length is taken from the signal component 111, 111' and multiplied by the Hanning window. Again, every half interval lengths later this is repeated and the thereby resulting signals, weighed by the windows functions, are again added together. This results in an optimized overall signal.

For this, the aforementioned multiplication by the sign of the second element of the coefficient components is further beneficial, and can also be essential, since any arbitrary (sign) variations in the signal components are avoided. These are very undesirable for the aforementioned optimization due to the adding procedure in the end which would otherwise lead to signals that are worse than before.

The aforementioned interval length can be chosen from 8 to 1024 picture periods, which is basically between 0.4 and 50 seconds. As a preferred interval length 1 to 2 seconds, more preferably 1.5 seconds, are chosen for cases with vigorous motion, which corresponds to at least one pulse-period. However, longer intervals may be preferred in a more static scenery.

By way of example, the present invention can be applied in the field of health care, e.g., unobtrusive remote patient monitoring, general surveillances, security monitoring and so-called life style environments, such as fitness equipment, or the like. Applications may include monitoring of oxygen saturation (pulse oximetry), heart rate, blood pressure, cardiac output, changes of blood perfusion, assessment of autonomic functions, and detection of peripheral vascular diseases. Needless to say, in an embodiment of the method in accordance with the invention, several of the steps described herein can be carried out in changed order, or even concurrently. Further, some of the steps could be skipped as well without departing from the scope of the invention. This applies in particular to several alternative signal processing steps.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. Device for extracting physiological information from remotely detected electromagnetic radiation emitted or reflected by a subject, comprising:

an interface for receiving a data stream derived from electromagnetic radiation detected at a location remote from the subject, the data stream comprising at least one sequence of signal samples representing a region of interest exhibiting a continuous or discrete characteristic signal including physiological information indicative of at least one at least partially periodic vital signal, and being comprised of at least two wavelength components, a transforming unit configured for determining and providing at least one coefficient component from the at least two wavelength components of the at least one sequence of signal samples to exclude information independent of the at least partially periodic vital signal and to include the physiological information indicative of the at least partially periodic vital signal, said at least one coefficient component being suitable for deriving at least one signal component by application to the at least one sequence of signal samples, a coefficient selection unit for selecting one coefficient component from the at least one coefficient component determined and provided by the transforming unit, a signal component unit for providing a signal component based on the selected coefficient component and the at least one sequence of signal samples, and a signal processing unit for providing the desired physiological information from the signal component.

2. Device as claimed in claim 1, wherein the coefficient selection unit is further configured for evaluating the at least one coefficient component based on a fixed and predetermined reference vector to select a coefficient component that is most influenced by the at least partially periodic vital signal.

3. Device as claimed in claim 2, wherein the transforming unit is further configured for determining and providing one coefficient component and the coefficient selection unit is further configured such that the coefficient component provided by the transforming unit is evaluated with respect to the fixed and predetermined reference vector.

4. Device as claimed in claim 3, wherein the transforming unit is further configured such that the determined and provided coefficient component is the coefficient component that results in the signal component with the highest variance.

5. Device as claimed in claim 3, wherein the coefficient selection unit is designed such that the evaluation is based on the angle between the provided coefficient component and the reference vector and further such that the coefficient component is selected if the angle is less than 45°.

6. Device as claimed in claim 1, wherein the transforming unit is further configured for determining and providing at least two coefficient components and the coefficient selection unit is further configured for selecting one of the at least two coefficient components by evaluating the coefficient components.

7. Device as claimed in claim 6, wherein the coefficient selection unit is designed such that the evaluation is based on the distance between the coordinates derived from the normalized vectors of the respective coefficient components and the coordinates of the reference vector, and the selection is based on the shortest distance.

8. Device as claimed in claim 6, wherein the coefficient selection unit is designed such that the evaluation is based on the angle between the provided at least two coefficient components and the reference vector and further such that the coefficient component with the smallest angle is selected.

9. Device as claimed is claim 2, wherein the predetermined reference vector is based on the skin tone of the subject.

10. Device as claimed is claim 2, wherein the interface is designed to receive RGB color data and the fixed vector is close to [−0.4, 0.8, −0.4], preferably close to [−0.41, 0.82, −0.41], more preferably close to [−0.408, 0.817, −0.408], and even more preferably close to [−0.4082, 0.8165, −0.4082].

11. Device as claimed in claim 6, wherein the coefficient components are realized as vectors having at least two elements and the coefficient selection unit is further designed such that the evaluation of the coefficient components is realized by comparing a relative value of a chosen element of a respective coefficient component vector with the relative values of the same element of the other coefficient component vectors and further such that the selection of the coefficient component vector is based on the highest relative value of the chosen element.

12. Device as claimed in claim 11, wherein the interface is designed to receive RGB color data and the chosen element corresponds to the green channel.

13. Method for extracting physiological information from remotely detected electromagnetic radiation emitted or reflected by a subject, comprising the steps of:

Receiving a data stream derived from electromagnetic radiation detected at a location remote from the subject, the data stream comprising a sequence of signal samples representing a region of interest exhibiting a continuous or discrete characteristic signal including physiological information indicative of at least one at least partially periodic vital signal, and being comprised of at least two wavelength components, determining and providing at least one coefficient component from the at least two wavelength components, said at least one coefficient component being suitable for deriving at least one signal component by application to the at least one sequence of signal samples to exclude information independent of the at least partially periodic vital signal and to include the physiological information indicative of the at least partially periodic vital signal, selecting one coefficient component from the at least one determined and provided coefficient component, providing a signal component based on the selected coefficient component and the sequence of signal samples, and providing the desired physiological information from the signal component.

14. A non-transitory computer-readable storage medium storing a program comprising instructions to cause a computer to implement the method as claimed in claim 13.

15. Device as in claim 2, wherein the fixed and predetermined reference vector is selected depending on a wavelength range of the electromagnetic radiation and on a vector selected to be representative of a surface coloration of the subject.

16. Device as in claim 15, wherein the vector selected to be representative of a surface coloration of the subject is selected to represent a mean skin tone based on measurements of a plurality of skin tones.

* * * * *